United States Patent [19]

Usrey

[11] Plant 5,084

[45] Aug. 9, 1983

[54] *JUNIPERUS SCOPULORUM* SELECTION

[75] Inventor: Bruce Usrey, Glendora, Calif.

[73] Assignee: Monrovia Nursery Company, Azusa, Calif.

[21] Appl. No.: 302,638

[22] Filed: Sep. 15, 1981

[51] Int. Cl.[3] ..... A01H 5/00

[52] U.S. Cl. ..... Plt./50

[58] Field of Search ..... Plt./50

*Primary Examiner*—James R. Feyrer

[57] ABSTRACT

A new and distinct selection of *Juniperus scopulorum* shrub (popularly known as a rocky mountain juniper). A unique sport that has a (1) prostrate habit; (2) foliage adhering closer to the stems; (3) higher rooting percentages.

2 Drawing Figures

DISCOVERY

This invention relates to a new and distinct variety of *Juniperus scopulorum* plant, a member of the Cupressaceae family. This new and distinct selection was discovered as a sport on *Juniperus scopulorum* 'Table Top Blue' plants grown at Monrovia Nursery Company, 18331 East Foothill Boulevard, Azusa, Calif. The sport was removed in November of 1979 and vegetatively reproduced by cuttings. Plants of this sport exist only within the boundaries of Monrovia Nursery and they have never been offered for sale or described in any publication.

REPRODUCTION

This new and distinct sport of *Juniperus scopulorum* is distinctly different from *Juniperus scopulorum* 'Table Top Blue', the plant on which the sport was found, therefore propagation is strictly vegetative. Due to its unique genetic makeup and appearance which is vastly different from the parent this plant has not been reproduced true from seed. Seedlings from this unique plant have not been observed.

BRIEF DESCRIPTION OF THE DRAWING

The photo at the top labelled invention shows the unique outward growth of the claimed plant 'Blue Creeper' the subject of this application. The photo at the bottom labelled parent depicts the young upright growth habit of the parent 'Table Top Blue'.

CHARACTERISTICS

This unique sport differs from the parent and other selections of *Juniperus scopulorum* in that is does not exhibit an erect growth habit. Rather our unique sport has a growth habit which is more prostrate and decumbent with branches growing horizontally and tending to rise at the tips of branches. This prostrate-like, decumbent habit is very unique in this species and creates an ornamental demand for this plant where other selections of this sport could not be utilized.

The second characteristic that makes this plant unique from its parent plant is the foliage. On our new sport the foliage is more tightly adpressed to the stem in both the adult and juvenile stage when compared with the parent plant. This gives our sport the appearance of having a softer and smoother looking foliage.

Third, our new and distinct sport exhibits a greater percentage of rooting in asexual propagation than other

*Juniperus scopulorum* selections propagated at Monrovia Nursery Company by the same methods. Of cuttings made on our new and distinct selection the average percentage of rooting is 75 to 85 percent. Whereas other *Juniperus scopulorum* selections propagated here have a rooting percentage of 65 to 70 percent. Our new and distinct sport selection shows a superior rooting percentage as compared to other *Juniperus scopulorum* selections.

DESCRIPTION

Below is a detailed description of the new variety, all color terminology is from the British Horticultural Color Charts.

Habit and size:

Evergreen conifer, a prostrate shrub with a decumbent growth habit; eventual size predicted to be 1½ to 2 feet in height and 6 to 8 feet in spread. The parent, 'Table Top Blue' also an evergreen conifer is, flat-topped and semi-spreading when mature with an eventual size of six feet in height and 8 feet in spread.

Flower:

The flower has not been observed.

Foliage:

*Juvenile.*—Size: 3/16 to ¼ inch long; 1/16 inch wide. Arrangement: Slightly spreading at a 45 degree angle, (compared with 'Table Top Blue' the selection it was growing on which has almost a 90 degree angle of its juvenile leaves. Glaucous Bloom: Present on new foliage and side of foliage adhering to the stem. Color: Juvenile with glaucous bloom — Ethyl Blue 548/3. Shape: Subulate in shape with an apiculate tip.

*Mature.*—Size: ⅛ inch long; 1/16 inch wide. Arrangement: Adhering closely to the stems. Glaucous Bloom: Covering foliage, lacking on outside of leaf. Color: Leaf surface without glaucous bloom — Spinach Green 0960/2. Leaf surface with glaucous bloom — Ethyl Blue 548/3.

Fruit: The fruit has not been observed.

I claim:

1. A new and distinct selection of *Juniperus scopulorum* as substantially shown and described, a selection characterized by a unique combination of a prostrate decumbent growth habit, foliage which adheres closer to the stem and higher rooting percentages.

* * * * *

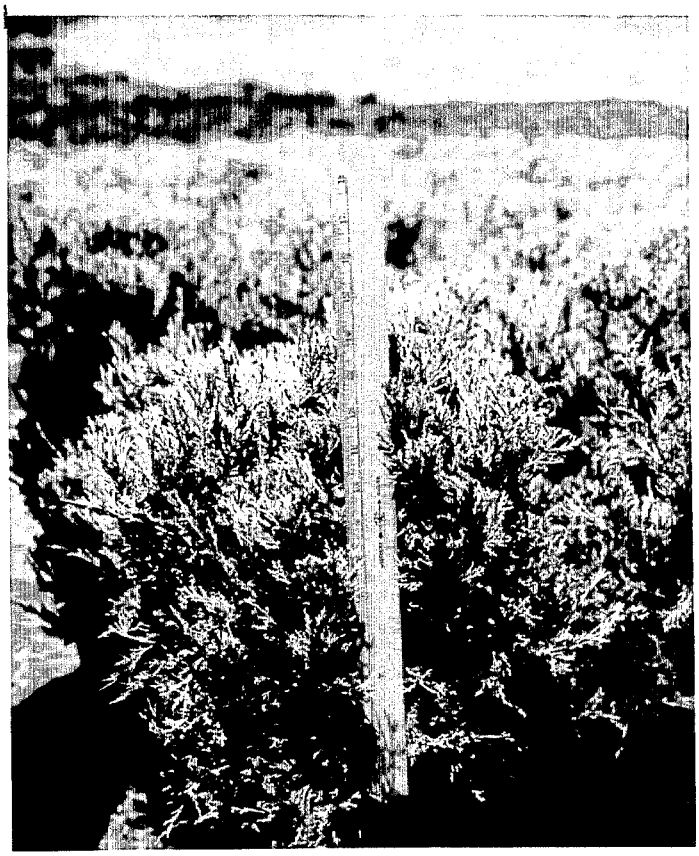

Invention
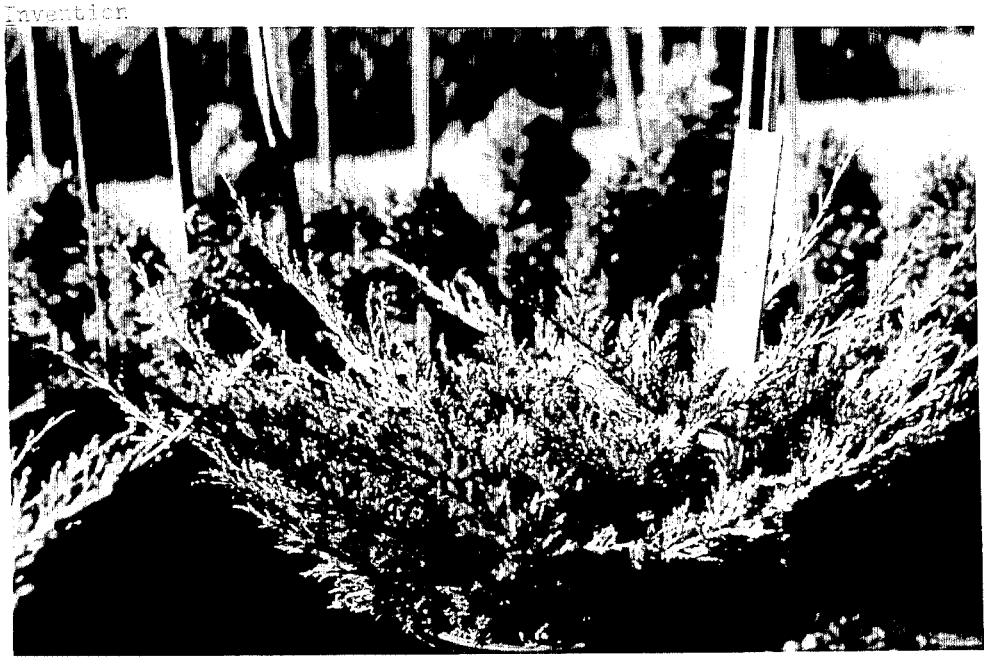
Parent